United States Patent
Ji et al.

(10) Patent No.: US 6,686,594 B2
(45) Date of Patent: Feb. 3, 2004

(54) ON-LINE UV-VISIBLE LIGHT HALOGEN GAS ANALYZER FOR SEMICONDUCTOR PROCESSING EFFLUENT MONITORING

(75) Inventors: Bing Ji, Allentown, PA (US); Robert Gordon Ridgeway, Quakertown, PA (US); Eugene Joseph Karwacki, Jr., Orefield, PA (US); Howard Paul Withers, Jr., Breinigsville, PA (US); Steven Arthur Rogers, Seoul (KR); Peter James Maroulis, Mertztown, PA (US); John Giles Langan, Pleasanton, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 149 days.

(21) Appl. No.: 10/003,223

(22) Filed: Oct. 29, 2001

(65) Prior Publication Data

US 2003/0098419 A1 May 29, 2003

(51) Int. Cl.⁷ .................................................. G01J 3/12
(52) U.S. Cl. ...................................... 250/373; 250/372
(58) Field of Search ............................. 250/373, 372, 250/336.1, 364, 468.28; 438/8, 16

(56) References Cited

U.S. PATENT DOCUMENTS

| | | | |
|---|---|---|---|
| 5,206,701 A | * 4/1993 | Taylor et al. ............... 356/325 |
| 5,281,816 A | * 1/1994 | Jacobson et al. ......... 250/339.05 |
| 5,545,897 A | * 8/1996 | Jack ....................... 250/339.13 |
| 5,812,403 A | 9/1998 | Fong et al. |
| 6,023,065 A | 2/2000 | Garver, Jr. et al. |
| 6,079,426 A | 6/2000 | Subrahmanyam et al. |
| 6,154,284 A | 11/2000 | McAndrew et al. |
| 6,240,117 B1 | 5/2001 | Gong et al. |

2002/0051132 A1 * 5/2002 Ohno et al. .................. 356/437

FOREIGN PATENT DOCUMENTS

WO    WO 98/40721    9/1998

OTHER PUBLICATIONS

V.M. Donnelly, "Optical Diagnostic Techniques for Low Pressure Plasmas and Plasma Processing", AT&T Bell Lab., pps. 1–46, 1989.*

European Patent Application No. 768525 by James McAndrew et al. for "System for Monitoring Chamber Exit Gases by Means of Absorption Spectroscopy, and Semiconductor Processing System Incorporating The Same", filed May 6, 1997.

Hideo Okabe, "Photochemistry of Small Molecules", John Wiley & Sons, Inc., 1978, pp. 185–187.

K.P. Huber et al., Molecular Spectra and Molecular Structure IV. Constants of Diatomic Molecules, Van Nostrand Reinhold Company Inc., 1979, pp. 106, 146, 148,214.

(List continued on next page.)

Primary Examiner—David Porta
Assistant Examiner—Christine Sung
(74) Attorney, Agent, or Firm—Geoffrey L. Chase

(57) ABSTRACT

An on-line halogen analyzer system and method of use for semiconductor processing effluent monitoring. The system includes sampling the effluent stream into an absorption cell, and passing UV-Visible light through the effluent sample in the cell. After passing through the sample the light is collected by a photo detector for real-time wavelength-selective absorption analysis. The system provides simultaneous determination of the concentrations of multiple halogen gases (e.g. $F_2$, $Cl_2$, $Br_2$, and $I_2$) in semiconductor processing effluent streams. The invention can be used for chemical vapor deposition (CVD) chamber cleaning endpoint determination and to improve fluorine utilization efficiency in remote plasma downstream CVD chamber cleaning processes.

43 Claims, 8 Drawing Sheets

OTHER PUBLICATIONS

W.R. Harshbarger et al., "A Study of the Optical Emission from an rf Plasma during Semiconductor Etching", Applied Spectroscopy, vol. 31, No. 3, (1977), pps. 201–207.

S. Raoux et al., "Remote microwave plasma source for cleaning chemical vapor deposition chambers: Technology for reducing global warming gas emissions", J. Vac. Sci. Technol, B 17(2), Mar./Apr. 1999, pps. 477–485.

C.T. Laush et al., "Continuous Real–Time Detection of Molecular Fluorine ($F_2$) Emitted As A By–Product of CVD And Etch Processes", Semicon West, pps. D1–D12 (2000).

D.A. Skoog, "Principles of Instrumental Analysis", Saunders College Publishing, Third Edition, pps. 161–179, 1971.

E.J. Karwacki Jr., et al., "Preparing a gas delivery system for excimer lasers with fluorine passivation of 316L stainless steel", Air Products and Chemicals Feb. 2001, p. 1–7.

A.L. Cabrera et al., "Surface analysis of copper, brass, and steel foils exposed to fluorine containing atmospheres", J. Vac. Sci, Technol. A 8(6), Nov./Dec. 1990, pps. 3988–3996.

* cited by examiner

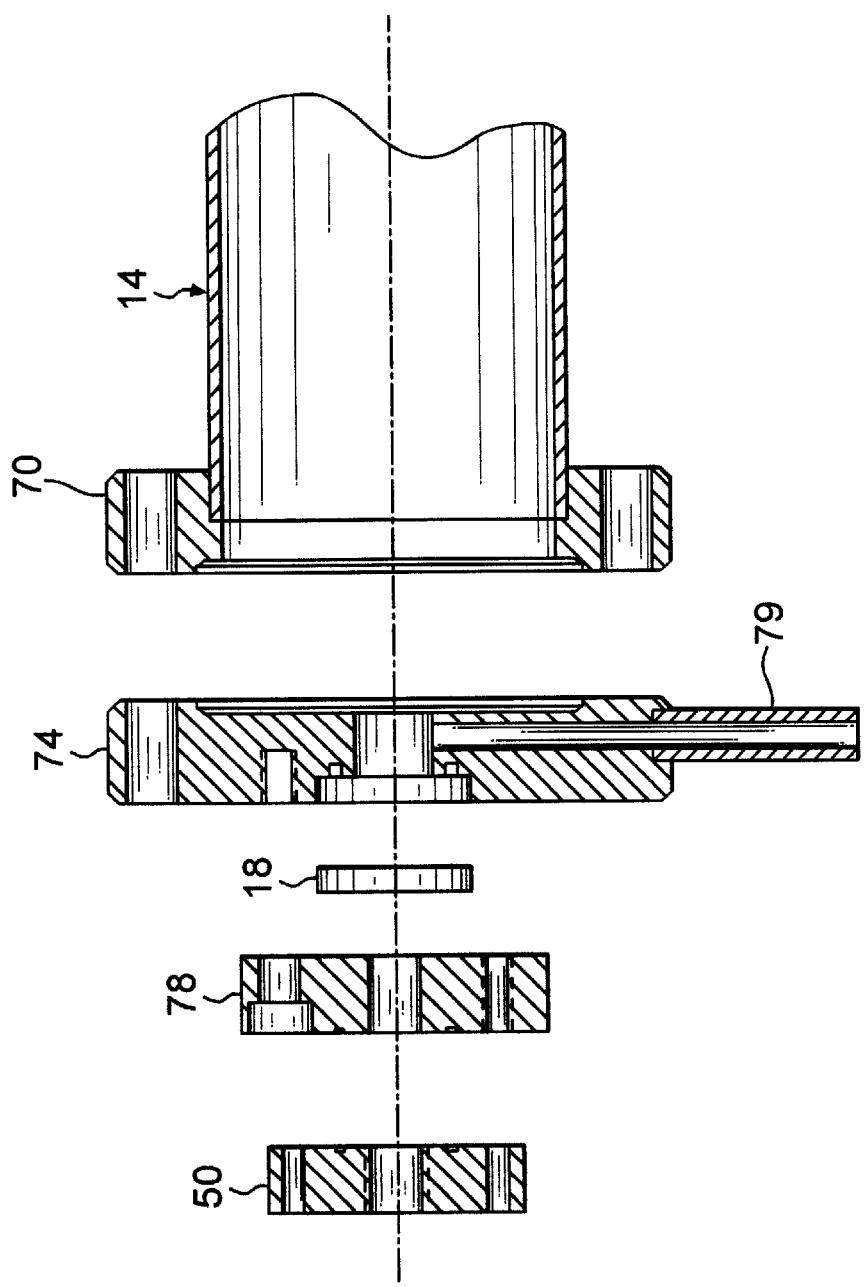

ON-LINE UV-VISIBLE LIGHT HALOGEN GAS ANALYZER FOR SEMICONDUCTOR PROCESSING EFFLUENT MONITORING

BACKGROUND OF THE INVENTION

1. Field of the Invention

The present invention pertains to a method and apparatus for analyzing effluent streams from various process tools used to make semiconductors, and in particular, to an on-line UV-Visible analyzer system for measuring the concentrations of homonuclear diatomic halogens ($F_2$, $Cl_2$, $Br_2$, and $I_2$) in a gas flow stream, and methods for using the analyzer system.

2. Description of the Related Art

In the manufacture of integrated circuits (IC), sequences of thin film deposition and etching steps are performed in order to construct several complete electrical circuits (chips) on monolithic substrate wafers. The general principles of IC manufacturing are described in a publication entitled Handbook of Semiconductor Manufacturing Technology, Y. Nishi and R. Doery editors, Marcel Dekker, New York, N.Y. 2000.

In a typical manufacturing sequence, molecular gases containing halogen atoms are often used in processes to remove materials, either from an integrated circuit substrate or, from the internal components of deposition equipment. The process that removes material from integrated circuit substrates is typically referred to as etching, while the process for removing deposits on the inner walls of the deposition tools is called chamber cleaning. Chamber cleaning is necessary to maintain the quality of the film produced in the deposition processes. Etching is necessary to produce the desired circuit structure on the substrates.

Molecular gases containing halogens are often used in film removal processes because reactions with certain critical substrate materials form energetically stable, gaseous byproducts. These byproducts evolve from the substrate or process tool surface. They are then easily removed from the process equipment by vacuum pumping. In a typical process step, silicon dioxide ($SiO_2$) is deposited as an electrical insulating layer on the surface of a silicon wafer for example, by a plasma enhanced chemical vapor deposition (PECVD) process. Other thermal deposition processes are known to produce semiconductor films. After removal of the wafer from the process chamber, residual $SiO_2$ remains on the inside of the process chamber and must be removed to prevent the formation of particles. In some processes, a gas containing fluorine such as $NF_3$ or $C_2F_6$ is converted in an electrical discharge plasma to atomic fluorine, according to the reaction:

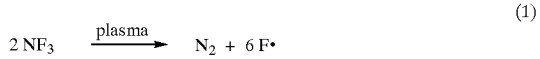

$$2 NF_3 \xrightarrow{plasma} N_2 + 6 F\cdot \quad (1)$$

This plasma can be generated between electrodes located in the deposition chamber. In this case, the process is termed "in situ plasma chamber cleaning". The plasma can also be generated upstream of the process chamber in which case it is termed "remote plasma downstream chamber cleaning".

Atomic fluorine reacts with $SiO_2$ to form volatile byproducts $SiF_4$ and $O_2$, according to the reaction:

$$SiO_{2(s)} + 4 F\cdot \longrightarrow SiF_{4(g)} + O_{2(g)} \quad (2)$$

A competing process is the recombination of atomic fluorine radicals to form molecular fluorine by the reaction:

$$2F\cdot \rightarrow F_{2(g)} \quad (3)$$

In most processes, the rate of reaction (1) is constant. As $SiO_2$ is removed from the process chamber, the rate of reaction (2) slows. This results in an increase in the number density of atomic fluorine in the process chamber and a subsequent increase in the rate of reaction (3). The time when the residual $SiO_2$ is completely removed from the internal components of the process chamber is called the "endpoint". The endpoint is marked by a plateau in the atomic fluorine (F.) number density and in the molecular fluorine ($F_2$) emission rate. Process control and optimization requires accurate determination of the endpoint to terminate the cleaning process.

For in situ plasma cleaning processes, an electrical discharge exists in the vicinity of the residual film being removed. There is an emission of light from the discharge at wavelengths specific to gases present in the discharge. One method for determining the endpoint of an in situ cleaning process is to monitor light emission from atomic fluorine. At the endpoint, this signal increases to a constant value due to the increase in fluorine concentration within the process chamber.

In remote plasma cleaning, the plasma is formed upstream of the process chamber containing the residual film. By the time the radical species flow into the process chamber, optical emission from the reactant gases ceases. Therefore, optical emission cannot be used to determine the endpoint.

Another method for determining the endpoint is to monitor the concentrations or flow rates of product species in the gas effluent from the process tool. In U.S. Pat. No. 6,079,426 patentees disclose a method to determine the endpoint by monitoring either the change in pressure in the process tool when the exhaust capacity is fixed, or the degree that the exhaust pump must be throttled to maintain a constant pressure. In other words, this method monitors the changes in the exhaust pump throughput. This method is only applicable to processes in which the number of atoms or molecules generated in the process changes by a measurable amount as endpoint is reached. Unfortunately, most of the chamber cleaning procedures use large amounts of inert diluent gases (e.g. Helium) in addition to reactive gases, hence the changes in the number of atoms or molecules generated by the plasma processes are greatly diluted by the large inert gas flow and may become too small to provide an accurate indicator of the end point.

Methods that directly monitor chemical species within the process effluent are more desirable from a process control perspective.

In U.S. Pat. No. 5,812,403 patentees disclose an infrared absorption endpoint monitor based on the absorption of infrared light by species present within the exhaust gas of a process tool. This endpoint detection method is specific to processes that form species that absorb infrared light in a specific band of infrared wavelengths. It is highly desirable to have a widely applicable system that can detect the endpoint following chemical vapor deposition of any material in which a molecular species containing a halogen is used as the reactant. A large number of deposition residues are removed by reactions with halogen-containing gases. These include tungsten, silicon, silicon dioxide, and silicon nitride. It is also desirable to have a system that is independent of the energy source used in the chamber cleaning process.

An IC process effluent stream may contain one or more homonuclear diatomic halogen gases. For example, $NF_3$, and $C_2F_6$ based chamber cleaning processes emit $F_2$ in the process effluent stream. Use of $ClF_3$ in chamber cleaning emits both Cl2 and F2. Use of fluorocarbons such as C4F8 and C4F6 etc. in dielectric plasma etching may emit F2. Use of HBr and BCl3 in conductor (for example, polysilicon and metals) plasma etching leads to emission of Cl2 and Br2. These homonuclear diatomic halogen gases (such as F2, Cl2, Br2, and I2) are highly toxic, reactive, and corrosive. The amounts of these halogen gases released from a semiconductor fabrication site cannot exceed government mandated limits. Therefore, homonuclear diatomic halogen gases must be quantified prior to release to the environment or an abatement system.

Typical instruments used to measure concentrations of effluent species in real-time include infrared and mass spectrometers. Both techniques have severe limitations in this application.

In U.S. Pat. No. 6,154,284, patentees disclose use of a tunable diode laser absorption spectrometer (TDLAS) to quantify species in an IC process effluent stream. TDLAS is a special kind of infrared spectrometer. Other types of infrared spectrometers include non-dispersive infrared (NDIR) and Fourier Transform Infrared (FTIR) types.

Infrared spectrometers determine the concentration of various species in a gas cell by measuring the decrease in the intensity of infrared radiation traversing the cell due to absorption. The degree of absorption is dependent on the concentration of each absorbing species. The pattern of infrared absorption as a function of wavelength, or "spectrum" is unique for each absorbing species. Absorption of infrared light generally results from the excitation of specific vibrational modes in the absorbing molecule. Not all vibrational modes, however, can be excited by infrared light. Those that do not absorb light are "infrared inactive". The single vibrational mode of homonuclear diatomic molecules, such as $N_2$, $O_2$, $F_2$, $Cl_2$, and $Br_2$ are infrared inactive. As a result, none of the homonuclear diatomic halogen molecules absorbs infrared radiation. Thus, they cannot be quantified using infrared spectroscopy.

Mass spectrometers determine the concentrations of various species in a gas sample by ionizing the sample by collisions with high energy (70 eV) electrons, then separating and detecting fragment ions. The pattern that an analyte fragments into is unique for most molecular species. The ion current for each fragment is dependent on the concentration of the analyte. Thus the concentration of the analytes can be determined from the fragment ion currents.

Mass spectrometry is typically performed in a high vacuum environment, preferably at pressures less than 10–6 Torr. Since the ionization and separation processes must be done in regions where the probability of collisions with other molecules over the measurement time is low, the vacuum pumps required to reduce the pressure to this level are large and require substantial time to set up. Due to their size, mass spectrometers with the required sensitivity are expensive to transport.

The sensitivity of the detector used in mass spectrometers is typically not stable over long periods of time. This requires that mass spectrometers be calibrated frequently to accurately measure the fragment ion current as a function of analyte concentration.

Halogen molecules are highly corrosive species. The presence of these species near the working components of mass spectrometers such as ion sources, detectors, and pumps causes their performance to degrade and eventually these devices cease to operate. These high performance components are expensive to refurbish or replace and leads to a higher cost of ownership for the analyzer.

C. T. Lauch, V. Vardaniar, L. Menchunor and P. T. Brown in a publication titled Continuous Real-Time Detection of Molecular Fluorine (F2) Emitted As a By-Product of CVD and Etch Processes, Semicon Southwest, Austin, Tex. October 2000, disclose a fluorine chemical sensor (FCS). In a fluorine chemical sensor, F2 oxidizes an organic substrate which then emits chemiluminescence to be detected by a photo multiplier tube (PMT). A fluorine chemical sensor cannot detect other homonuclear diatomic molecules such as Cl2, Br2, etc. because other halogen gases are not as oxidative as F2. On the other hand, other highly oxidizing species such as NF3 and O3 in the effluent stream may also react with the organic substrate and be falsely registered as F2. A fluorine chemical sensor response to $F_2$ concentration is nonlinear. In addition to $F_2$ concentration, a fluorine chemical sensor signal strength also depends on the mass flux to sensor surface area ratio. Therefore, effluent measurement must be made with the same mass flux as that of the calibration. This condition is sometimes difficult to satisfy due to changes in flow rates of slip stream sampling. A fluorine chemical sensor is suitable for low to moderate levels of $F_2$ concentrations only. High concentrations of $F_2$ may consume the organic substrate quickly and degrade its performance. Long term drift of the zero baseline and the signal response is also a concern when a fluorine chemical sensor is exposed to harsh corrosive gas streams.

In U.S. Pat. No. 6,023,065, the patentees disclose a method of using UV-Visible absorption spectroscopy to measure a bleaching agent, such as hydrogen peroxide ($H_2O_2$) and chlorine ($Cl_2$), dissolved in pulp delignification waste water. The method involves measurements in an aqueous solution, hence conventional UV-Visible spectrometers and sampling devices can be employed. The gaseous effluent streams in the IC manufacturing processes present unique and different challenges to sampling and quantification of toxic and corrosive species.

In view of the problems with prior art devices and methods, it was desirable to develop a device to measure the quantities of halogens in semiconductor effluent streams that is less costly to transport, does not require frequent calibration, does not degrade expensive equipment, is readily interfaced to semiconductor process tools, and can be easily and quickly set up. It was also desirable to have a system that can detect all the homonuclear diatomic halogen gases simultaneously, and in real-time within an IC process effluent stream. It was further desirable that such a system should be rugged and stable, and suitable for a wide range of analyte concentrations. Furthermore, it was desirable to have a system that provides accurate endpoint for an IC manufacturing process such as remote plasma downstream chamber cleaning. Such an endpoint detector should be independent of the kind of materials deposited during the CVD processes.

BRIEF SUMMARY OF THE INVENTION

According to one aspect, the present invention is a UV-Visible Light halogen gas analyzer system comprising a UV-Visible light source, an absorption cell, a fiber optic coupled spectrometer, and a computer, with mathematical relationships established between the light absorbance and the halogen concentrations. The system includes sampling for real-time on-line monitoring of halogen containing gases in IC manufacturing processing streams. In addition the system includes a slip-stream manifold for rapid and accurate sampling of process effluent streams.

A method and apparatus according to the invention provides accurate endpoint alternatives for IC manufacturing processes such as remote plasma downstream chamber cleaning.

Also the present invention pertains to an on-line sensor and method to monitor concentration of halogen species within a process effluent of a semiconductor manufacturing process to enable an operator to readily make changes to an operating parameter of the process such as, flow rates of reactants, electrode power, and process temperature.

Therefore, in one aspect, the present invention is a method for analyzing homonuclear diatomic halogen gases in a process effluent stream comprising the steps of: withdrawing a sample of the gas stream containing the halogen gases; introducing the sample of the gas stream into a sample cell having first and second ends containing windows to transmit UV-visible light through the sample; passing the UV-visible light through the sample cell and detecting light absorption by halogen gases in the cell; analyzing a selected absorption spectrum at selected wavelengths; and performing spectrum analysis to determine type and concentration of halogen gases present in the effluent stream.

In another aspect, the present invention is an apparatus for detecting the presence of a homonuclear diatomic halogen gases in a sample gas comprising in combination: a generally elongated sample cell having a first end and a second end with the first and second ends closed by UV-visible light transmitting windows/viewports; means to introduce a sample gas proximate a first end of the sample cell; means to remove the sample gas proximate the second end of the sample cell; means to pass a beam of UV-visible light through the cell from the first end of the cell to the second end of the cell; means proximate the second end of the cell to collect the UV-visible light and conduct the UV-visible light to a spectrometer to determine light intensities at differing wavelengths exiting the cell; and means to use the measured UV-visible light intensities to determine the presence and quantity of halogen gas in said sample gas.

In yet another aspect, the present invention is a method for detecting the endpoint of a clean operation wherein a halogen gas is used to clean contaminants from internal surfaces of a semiconductor process tool comprising the steps of: continuously withdrawing samples of an effluent gas stream from the semiconductor process tool; introducing the samples of the effluent gas into a sample cell having a first and second ends containing windows to transmit UV-visible light through the sample; passing the UV-visible light through the sample cell and collecting light passing through the cell; analyzing the light passing through the cell for absortion spectrums at wavelengths indicating the presence of the halogen gas in the sample of effluent gas; and using the spectrum to determine when a large increase in the amount of the halogen gas is present in a sample of effluent gas thereby indicating the tool is clean.

In a further aspect, the present invention is a method for controlling a semiconductor manufacturing process by monitoring the concentration of homonuclear diatomic halogen gases in a process gas stream comprising the steps of: withdrawing a sample of the gas stream containing said halogen gases; introducing said sample of the gas stream into a sample cell having first and second ends containing windows to transmit ultra violet and visible light through the sample; passing the light through the sample cell and detecting light absorption by halogen gases in the cell; analyzing a selected absorption spectrum at selected wavelengths; performing spectrum analysis to determine type and concentration of halogen gases present in the effluent stream; and using data from spectrum absortion to control the operating parameters of the process.

BRIEF DESCRIPTION OF SEVERAL VIEWS OF THE DRAWINGS

FIG. 2b is a left side elevational view of the absortion cell of FIG. 2a.

FIG. 3 is a partial exploded cross-section view of an absortion cell according to the present invention illustrating coupling of an optical fiber, window and gas inlet to the body portion of FIG. 2.

DETAILED DESCRIPTION OF THE INVENTION

Figure 1:
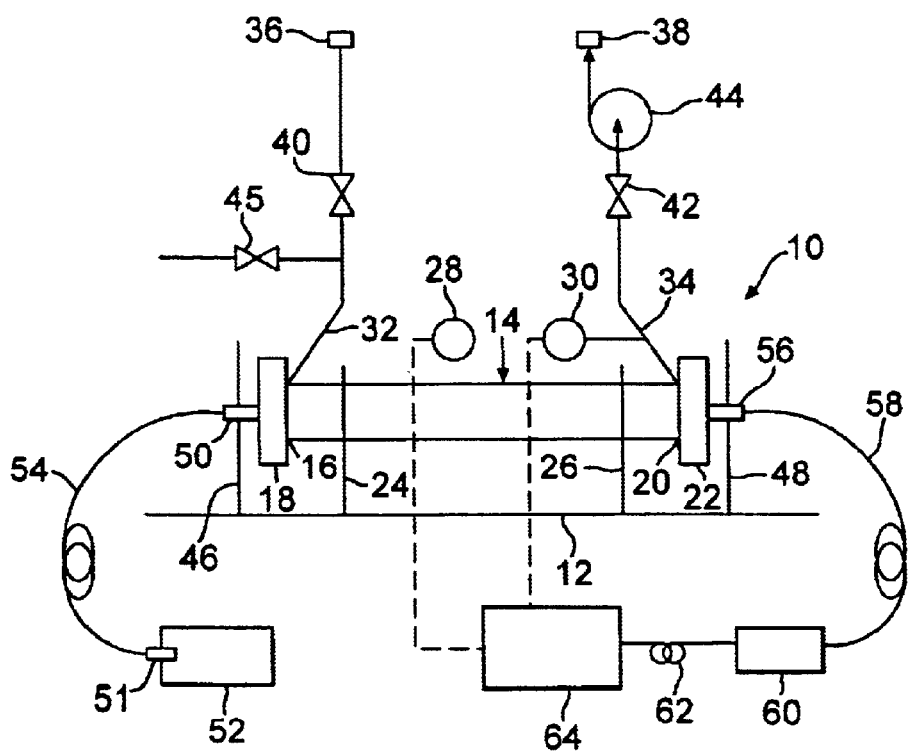
FIG. 1 is a schematic diagram of an on-line UV-Visible analyzer system according to the present invention.

The present invention utilizes absorption spectroscopy for detecting and quantifying gas phase halogen species. When light traverses through an absorbing medium, the attenuation (i.e., absorption) of light intensity is related to the concentration of an absorber as prescribed by Beer's Law represented by the equation:

$$\log\left(\frac{I_0(\lambda)}{I(\lambda)}\right) = A(\lambda) = \varepsilon(\lambda)lc \qquad (4)$$

where $I_0(\lambda)$ is the incident light intensity at wavelength $\lambda$, I is the transmitted light intensity at wavelength $\lambda$, $A(\lambda)$ is the absorbance at wavelength $\lambda$, $\varepsilon(\lambda)$ is the absorptivity of the specific molecule at wavelength $\lambda$, I is the optical path length, and c is the concentration of the absorbing molecule. Homonuclear diatomic halogen vapors ($F_2$, $Cl_2$, $Br_2$, and $I_2$) all absorb in the UV-Visible range of the spectrum between 200 and 600 nm. The optical path length I is fixed for a particular absorption cell setup. The absorptivity coefficient $\varepsilon(\lambda)$ is a constant characteristic of the molecule and the measurement wavelength. $\varepsilon(\lambda)$ can be accurately determined by calibrating the response of the system with a known reference sample. Once the system is calibrated, one can use Beer's Law (Equation 4) to determine the concentrations of the absorbing molecule. The light intensity ratio in Beer's Law allows the effect of changes in light throughput of the system to be cancelled out. Therefore, the system is robust under severe application conditions often encountered in semiconductor processing effluent streams. Minor coating of the windows with process residues and/or pitting will not cause unacceptable system response drift and hence no frequent re-calibration is needed.

When multiple absorbing species are present, the total absorbance is the sum of each constituent according to the equation:

$$A(\lambda) = \sum_i \varepsilon_i(\lambda) l c_i \qquad (5)$$

Spectral interference can occur if the molecules have overlapping absorption spectra. This case occurs when with multiple halogen gases are present in the gas stream. However, for halogen molecules, each has its unique absorption characteristics in terms of peak absorption wavelength, absorption bandwidth and band shape. These differences enable the combined absorption spectrum to be deconvolved into individual components by linear least squares fitting. Hence the concentrations of all the homonuclear diatomic molecules ($F_2$, $Cl_2$, $Br_2$, and $I_2$) can be determined simultaneously by spectral deconvolution.

The present invention provides a means for monitoring and controlling a chamber cleaning process on a thin film deposition or etching system. By monitoring the concentration of halogen present within the process effluent, changes can be readily made to operating parameters such as the flow rates of reactants, electrode power, and process temperature in order to maximize the efficiency of the process. Furthermore, a precise determination of the endpoint for the cleaning process can be made. This helps reduce the amount of cleaning gas utilized and lowers the amount of process emissions. The end result is higher equipment productivity and a lower overall cost-of-ownership for the manufacturing process.

FIG. 1 is a schematic representation of an apparatus 10, according to the invention. The apparatus 10 includes a base plate 12, which is used to support a sample cell 14. Sample cell 14 is generally constructed from stainless steel tubing which has been passivated by the appropriate halogen to be analyzed. For example, if fluorine gas is to be detected then fluorine passivation of the stainless steel tube would be appropriate. A first end 16 of sample cell 14 is closed by a window 18 and a second end 20 of cell 14 is closed by a window 22. Windows 18 and 22 are also called view ports and are fabricated from materials known to be transparent in the UV-visible range. For example, sapphire, calcium fluoride or magnesium fluoride are well known in the art.

Sample cell 14 is fixed to base plate 12 by cell holders 24 and 26. The temperature inside cell 14 and the absolute pressure of gases inside the cell 14 are measured by a suitable thermometer 28 and a suitable pressure gage 30. A gas inlet port represented by line 32 is connected to the first end 16 of cell 14. An outlet port represented by line 34 is connected to the outlet end 20 of the cell 14.

Gas line couplers 36 and 38 are used to connect the sample cell 14 to the process (effluent) sample inlet 32 and outlet 34 respectively. Valve 40 associated with gas line coupler 36 is used to control flow of sample gas into cell 14 and valve 42 is used to control removal of sample gas from the cell 14. Removal of gas from the sample cell 14 can be aided by a pump shown generally as 44. Valve 45 is utilized to introduce purging gas into the sample cell 14 as needed.

A pair of holders 46 and 48 are disposed proximate the windows 18 and 22 respectively to, in the case of support 46 position an optical fiber cable coupler 50 to direct light through window 18 and through sample cell 14 as will hereinafter be more fully explained. Optical fiber cable coupler 50 is connected to a light source 52 via an optical fiber cable 54. Light source 52 can be a broad band light source such as a D1000 deuterium lamp offered to the trade by Analytical Instruments Systems Inc. Support 48 is used to position a second optical fiber coupler 56 proximate the window 22 to receive light emanating from window 22 and conduct the light via optical fiber cable 58 to a spectrometer 60. Spectrometer 60 is in turn connected via a suitable electrical cable 62 to a spectrometer control, data acquisition and data analysis system 64.

A fiber optic coupled detector, which is a spectrometer that is coupled to an optical fiber cable, can be used, provided it has sufficient spectral resolution and signal sensitivity at the desired wavelengths. It can also be a set of photo detectors combined with appropriate band-pass filters and coupled to optical fibers. A preferred embodiment is a spectrometer coupled to an optical fiber. A more preferred embodiment is a fiber optic coupled spectrometer equipped with an array type detector, such as a photo-diode array (PDA) with or without an intensifier, or a charge-coupled-device (CCD) array detector. Array detectors provide simultaneous measurement of light absorbance at multiple wavelengths, thus enabling spectral band fitting and simultaneous detection of multiple species. In a yet more preferred embodiment, an Ocean Optics S2000 fiber optic coupled CCD array spectrometer is used as detector (60). There are 2048 pixels in the CCD array inside an S2000 spectrometer. This allows determination of absorbance $A(\lambda)$ at over 2000 wavelengths simultaneously.

Photo detectors usually have some low levels of dark signal current. In other words, a detector has non-zero output without any incident light. Although generally very small, detector dark signal current can distort the measured absorbance in some cases. Furthermore, detector dark signal current varies with temperature. Small changes in ambient temperature can cause small changes in the dark current, which again, causes small drifts in the absorption measurement. Because of temperature dependence, a static baseline correction (or calibration) cannot fully eliminate the effect of the dark current. Instead, real-time dynamic subtraction of the dark current is needed. In one embodiment of the invention, one can take advantage of the dark current monitoring feature of the Ocean Optics S2000 to dynamically subtract the dark signal current in real-time before computing the light absorbance.

To fully take advantage of array detectors, one can use pixel binning. In other words, adjacent pixels are combined into a band, and the central wavelength of the band is used for analysis. This is called "pixel binning". Pixel binning enhances signal-to-noise ratio without taking a lot of signal averaging. This method enables fast and sensitive detection of weak absorbance signals. This method is particularly useful for endpoint detection of semiconductor processes since $F_2$ concentration can be small and changes in low level absorbance must be detected rapidly in such applications.

In operation the gas line couplers 36, 38 are used to connect the sample cell to the semiconductor processing effluent stream(s). With valve 45 closed and valve 42 opened and with pump 44 operating, gas samples are continuously taken through the cell 14 and then returned to the processing effluent stream via gas coupling device 38. The coupling devices 36, 38 can be fitted with various adapters to fit on various effluent stream lines which would be dictated by the particular semiconductor processing process or equipment.

UV-visible light is transmitted from the light source 52 through optical fiber cable 54 and optical fiber cable coupling device 50 to the sample cell. The output of the light is collimated and aligned via the optical fiber cable coupler 50. The light then travels through the sample cell 14 via the window 18 and interacts with halogen species in the effluent sample which is contained in the cell 14. At end 20 of sample cell 14, UV-visible light is collected via optical fiber cable coupler 56 and transmitted via optical fiber cable 58 to the spectrometer 60.

Holders 24, 26, 46 and 48 are made to be adjustable on the base plate 12 to provide horizontal and angular flexibility in the installation and alignment of the optical fiber cable couplers 50 and 56. Optical fiber cable couplers 50 and 56 can be adjusted for optimal beam collimation, and if needed, for light intensity attenuation to void saturation of the CCD array detectors in the spectrometer. Light intensity attenuation can also be achieved by adjusting an optical fiber cable coupler 51 which is installed at the output of light source 52.

The throttle valve 40 can be used to control the gas pressure inside the sample cell. The absolute pressure gauge is installed close to the gas exit port (34) to ensure accurate measurement of the pressure inside the sample cell 14. This arrangement allows absorbance measurement at any pressure without re-taking the calibration data. Absorbance measurement can be done at reduced pressure to avoid deviation from Beer's law at high absorbance (for example, greater than 1.0 AU). This technique extends the upper detectable concentration limit at a fixed cell length.

Figure 2A:
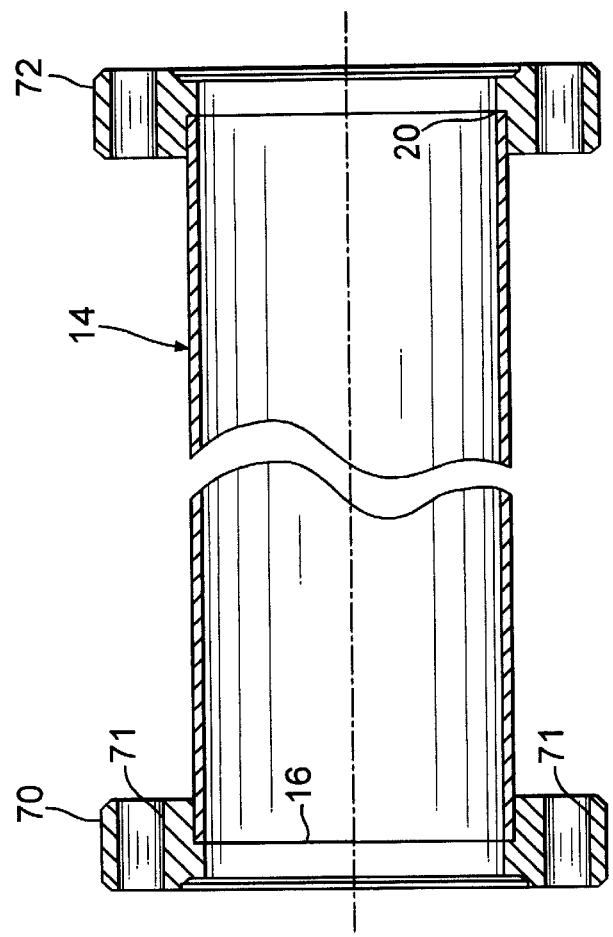
FIG. 2a is a cross-sectional view of the body portion of an absortion cell according to the present invention.

FIG. 2a is a cross-sectional view of an absorption cell suitable for use in the present invention. Cell 14 is fabricated from stainless steel and has fitted on ends 16, 20, window adaptors or flanges 70, 72. The optimal length of the cell (l) is determined by the concentration of the halogen molecules and the absorbance at the desired wavelengths. The internal volume of the cell should be optimized for minimal gas residence time and sufficient rigidity. Halogen gases are corrosive, and may adsorb onto the internal metal surfaces. The materials of construction for the absorption cell must be compatible with halogen gases. In one embodiment of the invention, the gas cell is made of stainless steel. The internal surfaces of the absorption cell can be passivated by a dilute fluorine mixture prior to its first use. Such passivation ensures fast, accurate, and stable measurement of halogen gases in an effluent stream.

Figure 2B:
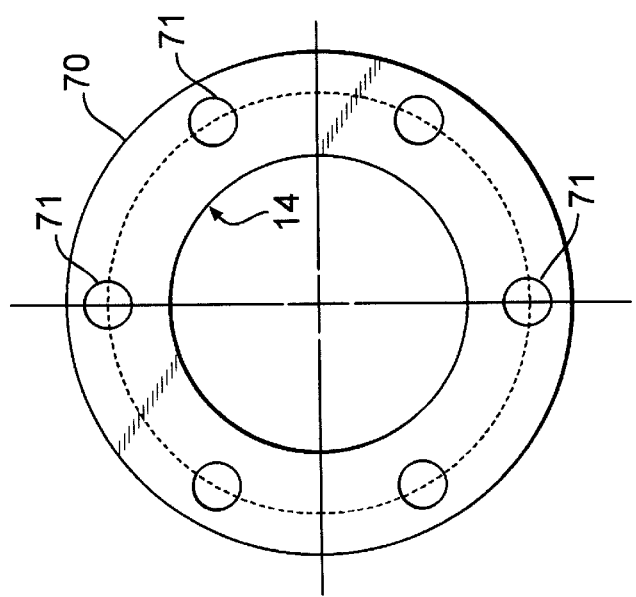

FIG. 2b is a left elevational view of the cell 14 showing details of apertures or holes 71 spaced equally around the face of flange 70 so that the cell 14 can be mated to the necessary auxiliary equipment as herein described.

FIG. 3 is a cross-sectional view of the left end of cell 14. A window flange 74 is fixed to flange 70 by bolts or other known techniques so that there is a gas tight seal between the window flange 74 and flange 70. Window flange 74 includes a central recess to receive and position window 18. A gas inlet 79 is fixed to window flange 74 for conducting sample gas into cell 14. Window 18 is held in place by window holder 78 adapted to assure a gas tight sealing of the window 18 in window flange 74. Outwardly of window holder 78 and fixed thereto is an optical fiber cable coupler holder 50. The opposite end 20 of cell 14 is fitted with flanges, window, window holder and an optical fiber cable coupler in a like manner. For dynamic real-time determination of halogen concentrations in a gas stream, dead volume must be eliminated in the absorption cell. As shown in FIG. 3, the absorption cell 14 dead volume is eliminated by positioning the sample inlet 79 on the edge of the window flange 74. In a similar manner the sample outlet would be placed on the other end of cell 14. In FIG. 1 the position of the inlet is shown as 32 and the outlet as 34.

The optical windows must have good transmission in the UV and Visible wavelength range (200-850 nm), and must be compatible with halogen gases. In one embodiment of the invention, sapphire or calcium fluoride (CaF2) flats are used as the windows. Chemically compatible elastomer (such as Kel-rez or Viton) O-rings can be used for leak-free seals. The windows (18, 20) are held against the window flanges (e.g. flange 74) by the window holder (78). The optical fiber cable coupler (50, 56) can be tilted relative to its window holder to align the transmitting and receiving angles of the light beam. Tilt adjustment in the coupler holders and collimating lens focus adjustment in the fiber cable coupler itself provide a means to optimize the light throughput of the absorption cell.

Beer's law prescribes the mathematical relation between the optical absorbance and the absorbent concentration $c_i$, i.e., the molecular number density of the absorbing molecules. Molecular number density is related to gas pressure and temperature as prescribed by the ideal gas law in the following equation:

$$c_i = \frac{f_i P N_0}{RT} \qquad (6)$$

where $c_i$ is the number density (concentration) of a halogen gas, $f_i$ is the molar fraction of the gas, P is the total pressure in the cell, $N_0$ is Avogadro constant, R is the ideal gas constant, and T is absolute temperature of the gas (in Kelvin). A temperature sensing thermal couple (28) and pressure sensor (30) are mounted on the absorption cell. The temperature and pressure readouts can be fed into the laptop computer (64) to convert $c_i$ to partial pressure $P_i$ for the said halogen gas.

Figure 4:
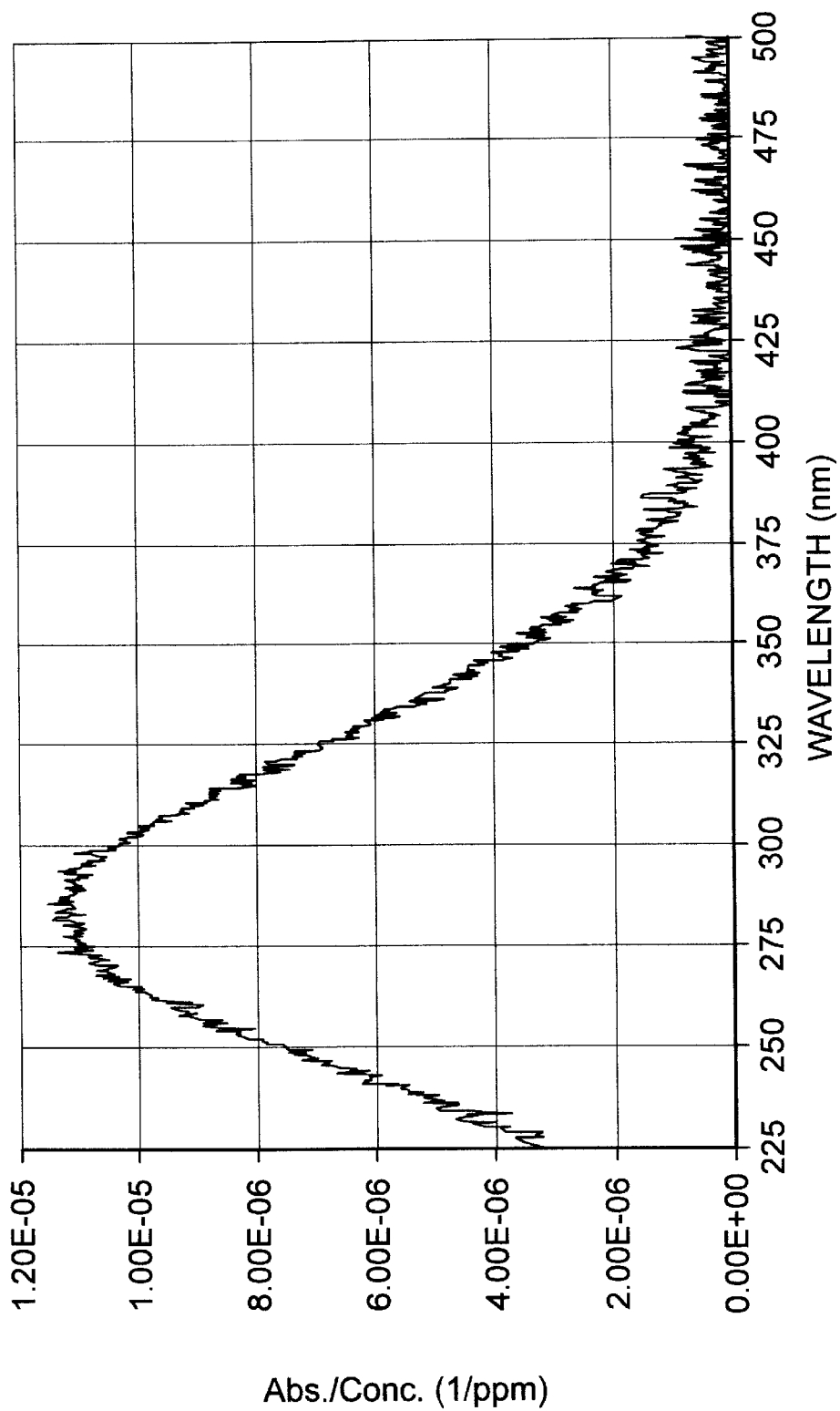
FIG. 4 is a plot of absorbance against wavelength for fluorine (F2) measured with the apparatus of FIG. 1.

FIG. 4 is a plot of fluorine ($F_2$) absorption spectrum from data taken by one embodiment of the invention. The absorption spectrum results from the transition from the $X^1\Sigma_g^+$ ground state to the dissociative $A^1\Pi_u$ excited state. The transition is continuous, ranging from 200 to 400 nm, peaking around 285 nm. It should be noted that if absorption at more than one wavelength is measured, the calculation based on Equation (4) is over-determined. Thus multivariate calibration (e.g., Classical Least Squares, Inverse Least Squares, or Partial Least Squares) can be used to calculate the most statistically significant result. Such multivariate analysis can be combined with the above pixel binning method. Table 1 is an example of the bands used for fluorine analysis.

TABLE 1

Bands Used in Analysis of Fluorine

| Band | Band Center Wavelength (nm) | Bandwidth (nm) | Bandwidth (pixels) |
|---|---|---|---|
| A | 230 | 20 | 53 |
| B | 255 | 30 | 81 |
| C | 285 | 30 | 81 |
| D | 315 | 30 | 81 |
| E | 345 | 30 | 81 |
| F | 445 | 30 | 81 |

Figure 5:
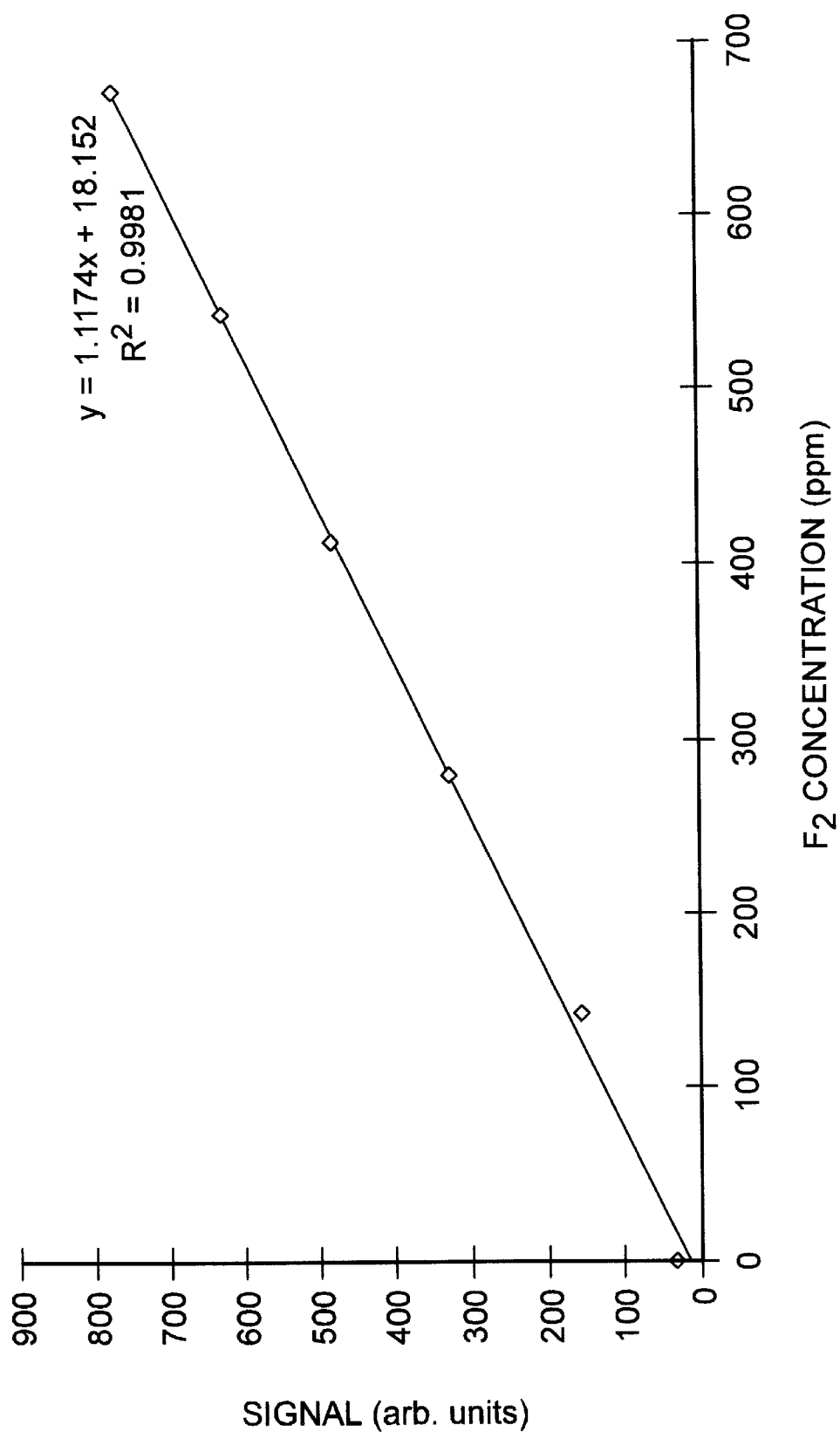
FIG. 5 is a plot of signal strength against fluorine concentration measured with the apparatus of FIG. 1.

Using the band analysis listed in Table 1, the responses of the system to low levels $F_2$ was tested and plotted in FIG. 5. Excellent sensitivity and linearity is shown by the data plotted in FIG. 5.

Figure 6:
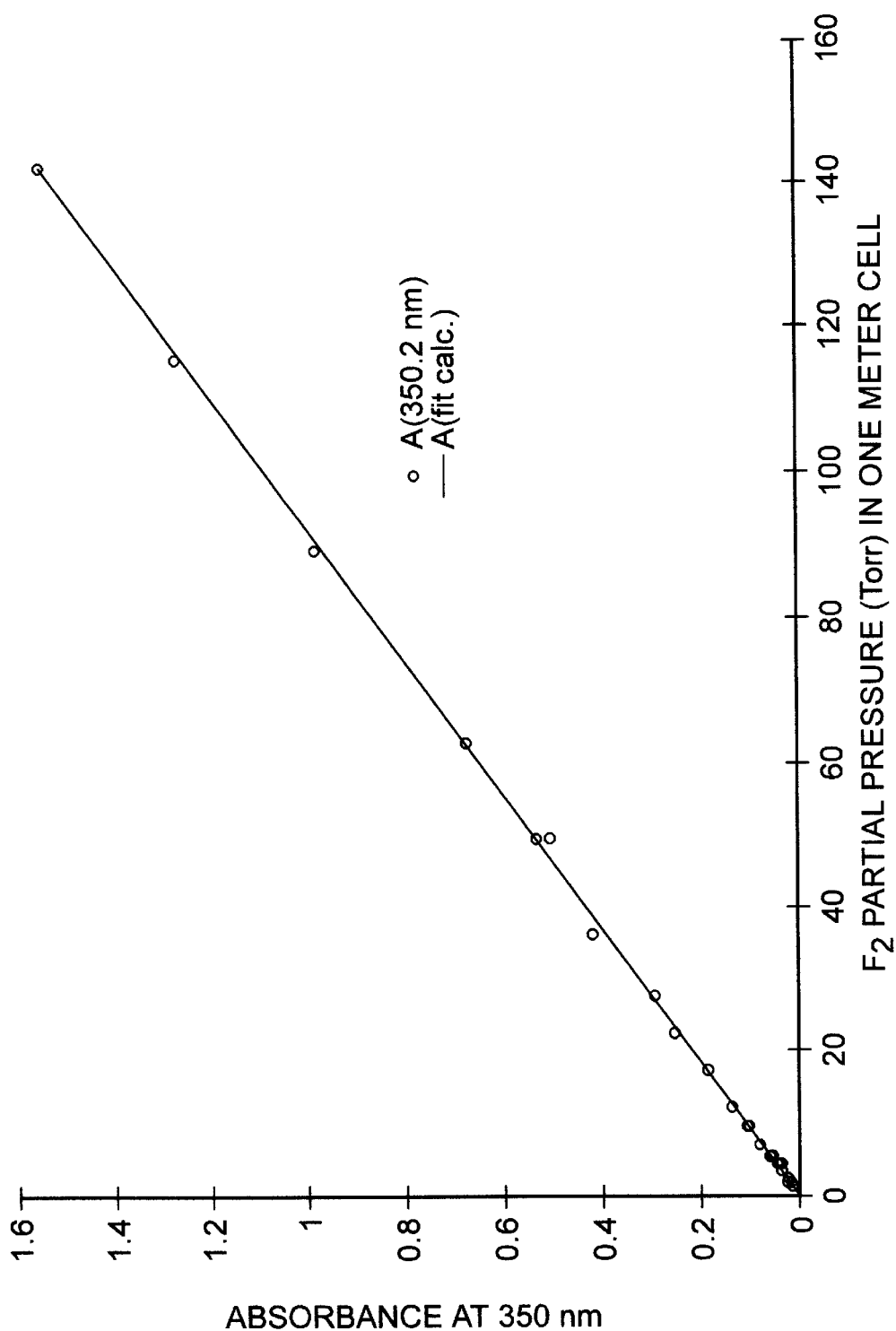
FIG. 6 is a plot of absorbance at 350 nanometers against partial pressure of fluorine measured by the apparatus of FIG. 1.

When high levels of $F_2$ are present in the absorption cell, the measured absorbance may deviate from linearity as prescribed by Equation (4) with strong absorption around the peak wavelength (285 nm). This generally occurs when the absorption exceeds 1.5 absorbance units, leading to erroneous determination of the fluorine concentration. This problem is solved by avoiding the peak absorption wavelength. Instead, one can analyze the data at weaker absorption wavelengths (i.e., at the "wings" of the absorption spectrum). For example, one can take the absorbance data at 350 nm to detect high levels of $F_2$ concentrations. The result is shown in FIG. 6. By taking the much weaker absorbing band at 350 nm, the linearity range (i.e., the validity range of Beer's law) can be greatly extended.

By proper choice of absorption cell length, analysis band wavelengths, and pixel binning, the system can determine halogen gas concentrations over four orders of magnitude. Operating the cell at different pressures, and/or using cells with different lengths can further extend the range of detectable halogen gas concentrations.

For on-line analysis of semiconductor processing effluents, rapid and accurate sampling must be incorporated into the system. One embodiment of the invention employs slip-stream sampling as shown schematically in FIG. 7. In a typical semiconductor fabrication facility, effluent gases exiting from a reactor pump station 90 are often diluted with large flows of inert purge gases such as nitrogen represented by arrow 92. Part of the nitrogen diluted effluent stream is taken at sample point (94). The slip-stream gas sample is pulled through the absorption cell (14) by a sample pump (96) and returned to the effluent pipeline at return point (98). An upstream throttle valve (100) is used to control sampling flow rate. A downstream throttle valve (102) is used to control the gas pressure in the cell. Precise adjustment of valves (100) and (102) ensures fast and accurate sampling, and optimal pressure for detection sensitivity. The spectrometer can be operated in time-acquisition mode. The absorbance at the six selected bands outlined in Table 1 can be taken consecutively. The data is processed by the laptop computer and halogen gas concentrations in the effluent stream can be measured in real-time by the on-line analyzer system of the present invention.

Figure 8:
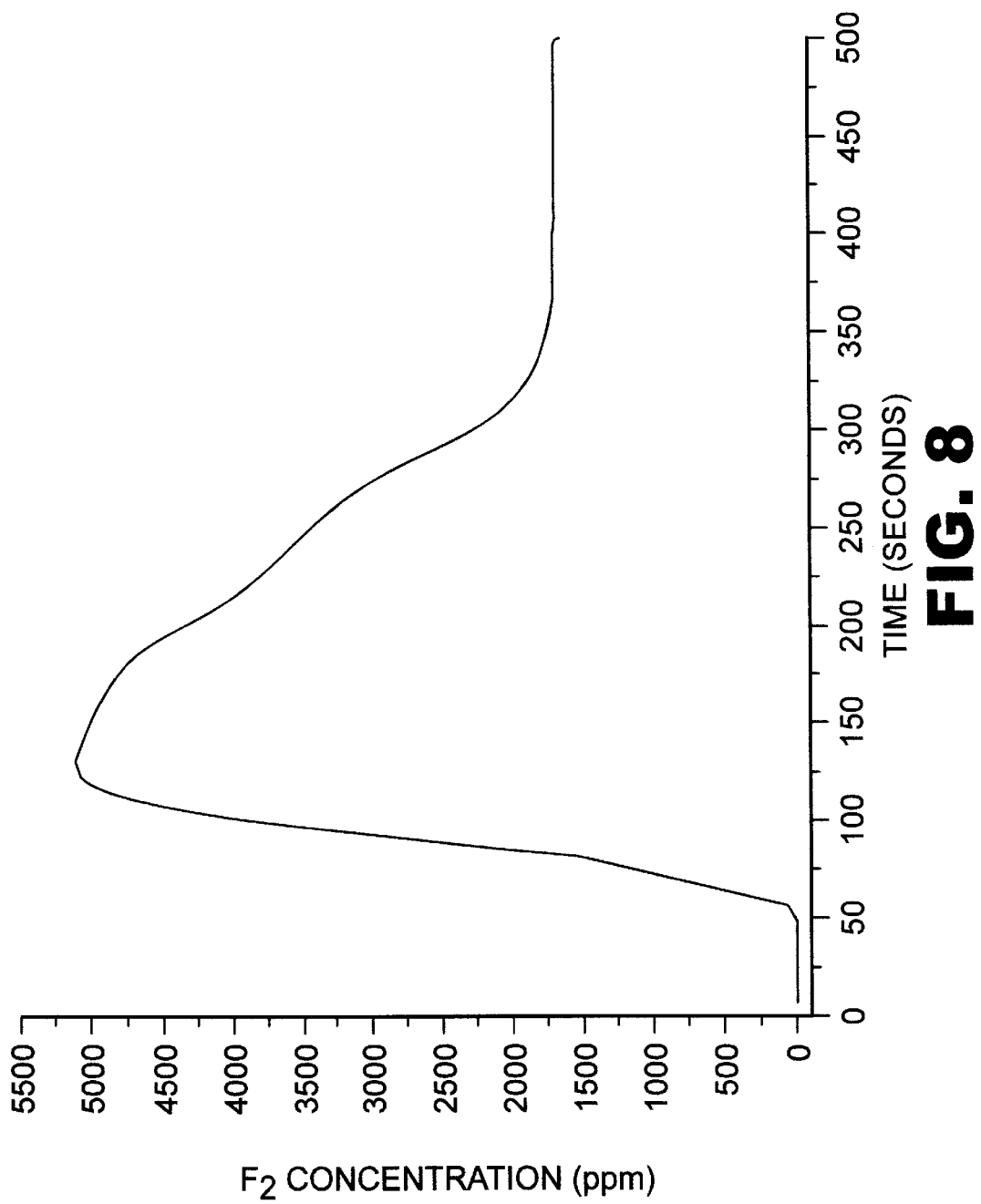
FIG. 8 is a plot of fluorine concentration against time measured by the apparatus of the present invention.

FIG. 8 is an example of time evolution of $F_2$ emission rate in a $C_2F_6$—$O_2$ plasma effluent stream. To obtain the data plotted in FIG. 8 a single crystalline silicon wafer coated with a layer of $SiO_2$ film was etched by the plasma. When the plasma was first turned on, relatively high levels of $F_2$ were emitted in the effluent. As the $SiO_2$ film was partially etched away, the silicon surface was gradually exposed to the plasma. Since silicon reacts with fluorine faster than $SiO_2$, more fluorine is consumed in the plasma and hence less $F_2$ is emitted into the effluent. When the $SiO_2$ film is completely cleared, a steady state of fluorine concentration is reached. The turning point, at about 300 seconds, in FIG. 8 marks an endpoint for the $SiO_2$ etch process. Therefore, the system according to the present invention can be used for endpoint detection in semiconductor processing.

The same method can be employed to determine the endpoint of a remote plasma downstream chamber cleaning process. As discussed above, a steady state (in this case, a plateau) of $F_2$ emission rate accurately indicates the endpoint. A plateau of $F_2$ emission rate can be identified as an inflection point in the $F_2$ concentration-time evolution curve. Mathematically the plateau turning point can be identified as zero first derivative or zero slope point. A laptop computer equipped with the data acquisition-analysis software can easily perform this data processing in real-time to detect the endpoint.

Figure 7:
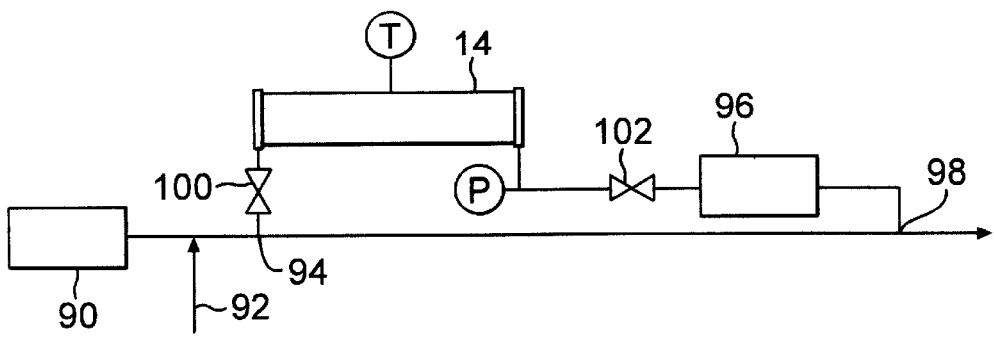
FIG. 7 is a schematic representation of a slip-stream effluent sampling system according to the present invention.

In some cases, the large nitrogen purge flow may attenuate the sudden change in fluorine concentration exiting from the reactor. Semiconductor fabrication facilities often use multistage dry pumps (such as an Edwards QDP pump and Pfeiffer Unidry pump) as the backing pumps for the reactor high vacuum pumps (such as turbo molecular pumps or Roots blower pumps). Large flows of inter-stage nitrogen purge gas is often injected into these dry pumps. These inter-stage purge gas flows may also attenuate the sudden change of the fluorine concentration exiting from the reactor. A further potential shortcoming of the downstream sampling as shown in FIG. 7 is that there is a time lag for the fluorine gas to travel from the reactor to the pump station. Depending on individual equipment setup in a fabrication site, there can be a significant distance between the reactor and the pump station. Significant gas travel time lag could cause delayed endpoint detection, if the halogen gas detector is installed downstream to the backing pump as shown in FIG. 7.

Figure 9:
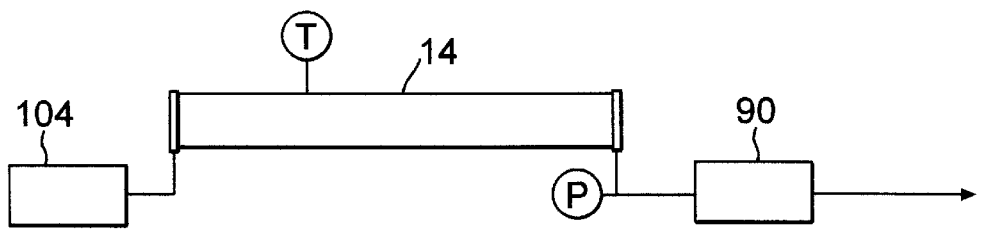
FIG. 9 is a schematic representation illustrating integration of a plasma processing system with an on-line analyzer according to the present invention.

FIG. 9 is a schematic representation of an embodiment of the invention made to overcome these shortcomings by inserting the sample (absorption) cell (14) between the reactor (104) and the reactor pump station (90). Alternatively, the absorption cell can be installed between the high vacuum pump and the backing pump when the high vacuum pump is connected directly to the reactor. This embodiment enables rapid detection when the $F_2$ emission rate from the reactor chamber changes. It also eliminates the time lag due to effluent gas travel and dilution interference from purge gas flows. It is therefore particularly valuable for endpoint detection in remote plasma downstream chamber cleaning.

Thus the present invention provides a device or apparatus to measure the quantities of halogens in semiconductor effluent streams that is less costly to transport, does not require frequent calibration, does not degrade expensive equipment, and is easily and quickly set up. The present invention provides an apparatus that can detect all the homonuclear diatomic halogen gases simultaneously, and in real-time within an IC process effluent stream. The apparatus or system according to the invention is rugged and stable, and suitable for a wide range of analyte concentrations. The system and method of the invention provides accurate endpoint for an IC manufacturing process such as remote plasma downstream chamber cleaning independent of the kind of materials deposited during the CVD processes.

Having thus described our invention what is desired to be secured by Letters Patent of the United States is set forth in the appended claims which should be read without limitation:

What is claimed is:

1. A method for analyzing homonuclear diatomic halogen gases in a process effluent stream comprising the steps of:
    withdrawing a sample of said gas stream containing said halogen gases;
    introducing said sample of said gas stream into a sample cell having first and second ends containing windows to transmit ultra violet and visible light through said sample;
    passing said light through said sample cell and detecting light absorption by halogen gases in said cell;
    analyzing a selected absorption spectrum at selected wavelengths; and
    performing spectrum analysis to determine type and concentration of halogen gases present in said effluent stream.

2. A method according to claim 1, including the step of using a spectrometer control, data acquisition and data analysis system to analyze said absorption spectrums.

3. A method according to claim 2, including the step of using one of a personal computer or a notebook personal computer with an A/D card to analyze said absorption spectrums.

4. A method according to claim 1, including the step of fabricating said sample cell from a fluorine passivated stainless steel tube with windows/viewports known to be transparent in the UV-visible range disposed on either end of said tube.

5. A method according to claim 4, including the step of monitoring and controlling temperature and pressure inside said cell.

6. A method according to claim 1, including the step of withdrawing one of, a part or a substantial part of the effluent flow from the effluent pipeline as said sample.

7. A method according to claim 6, including the step of extracting an effluent sample via a slip-stream sampling system through a sampling pump.

8. A method according to claim 7, including the step of controlling extraction flow rate and cell gas pressure by an upstream throttle valve and a downstream throttle valve.

9. An apparatus for detecting the presence of a homonuclear diatomic halogen gases in a sample gas comprising in combination:

a generally elongated sample cell having a first end and a second end with said first and second ends closed by visible and UV light transmitting windows/viewports;

means to introduce a sample gas proximate a first end of said sample cell;

means to remove said sample gas proximate said second end of said sample cell;

means to pass a beam of UV and visible light through said cell from said first end of said cell to said second end of said cell;

means proximate said second end of said cell to collect said light and conduct said light to a spectrometer to determine light intensities at differing wavelength exiting said cell; and means to use said measured light intensities to determine the presence and quantity of halogen gas in said sample gas.

10. An apparatus according to claim 9, wherein said sample cell is fabricated from a passivated stainless steel tube.

11. An apparatus according to claim 9, wherein said visible and UV light transmitting windows/viewports are one of sapphire or calcium fluoride.

12. An apparatus according to claim 9, wherein said means to pass said UV and visible light through said cell includes a first optical fiber coupler disposed proximate said window on said first end, said optical fiber coupler coupled to an optical fiber cable connected to a broad band light source.

13. An apparatus according to claim 9, wherein said means proximate said second end of said cell includes a second optical fiber coupler disposed proximate said window on said second end, said optical fiber coupler coupled to an optical fiber cable connected in turn to a spectrometer.

14. An apparatus according to claim 9, including means to measure temperature and pressure in said sample cell.

15. An apparatus according to claim 9, wherein said means to determine presence and quantity of halogen gas includes a spectrometer control data acquisition and data analysis system being one of a PC or a PC with an A/D card.

16. An apparatus according to claim 9, wherein the said absorption cell has gas inlet and outlet ports on flanges supporting said windows to eliminate dead volumes.

17. An apparatus according to claim 12, wherein said optical fiber coupler has a holder for tilting and collimating adjustment to attain optimal light throughput.

18. An apparatus according to claim 9, wherein said sample cell is fabricated from halogen compatible materials, and is passivated prior to service to facilitate rapid determination of halogen gases in said sample gas.

19. An apparatus according to claim 9, wherein said system utilizes UV-Visible grade optical fibers to transmit light from said light source into the cell, and from said cell into a photo detector.

20. An apparatus according to claim 9, wherein said system utilizes a fiber optic coupled CCD array spectrometer to measure absorption spectra.

21. An apparatus according to claim 9, wherein said system utilizes a laptop computer for instrument control, data acquisition, and signal processing.

22. An apparatus according to claim 9, including means to dynamically subtract a photo detector dark signal current before conducting absorbance calculation.

23. A method for detecting the endpoint of a clean operation wherein a halogen gas is used to clean contaminants from internal surfaces of a semiconductor process tool comprising the steps of:

continuously withdrawing samples of an effluent gas stream from said semiconductor process tool;

introducing said samples of said effluent gas into a sample cell having a first and second ends containing windows to transmit light containing visible and ultra violet light through said sample;

passing said light through said sample cell and collecting light passing through said cell;

analyzing said light passing through said cell for absortion spectrum at wavelengths indicating the presence of said halogen gas in said sample of effluent gas; and using said spectrum to determine when a large increase in the amount of said halogen gas is present in a sample of effluent gas thereby indicating said tool is clean.

24. A method according to claim 23, including the step of using a spectrometer control, data acquisition and data analysis system in combination with said spectrometer to record measured absorbance spectrums.

25. A method according to claim 24, including the step of using a personal computer or a notebook personal computer with a A/D card as said spectrometer control, data acquisition and data analysis system.

26. A method according to claim 23, including the step of fabricating said sample cell from a fluorine passivated stainless steel tube with sapphire windows/viewports disposed on either end of said tube.

27. A method according to claim 23, including the step of monitoring and controlling temperature and pressure inside said cell.

28. A method according to claim 23, including the step of determining one of, $F_2$ emission rate plateau, or the zero slope in the $F_2$ concentration-time plot to indicate the endpoint.

29. A method according to claim 23, including the step of using a $NF_3$ based remote plasma downstream chamber cleaning process.

30. A method for analyzing halogen gases ($F_2$, $Cl_2$, $Br_2$, and $I_2$) exiting from a semiconductor processing reactor according to claim 23, where the halogen analyzer is incorporated between the reactor and the pump station prior to any purge gas dilution.

31. A method for analyzing halogen gases ($F_2$, $Cl_2$, $Br_2$, and $I_2$) exiting from a semiconductor processing reactor according to claim 23, where the halogen analyzer is incorporated between the reactor high vacuum pump and the backing pump prior to any purge gas dilution.

32. A method for semiconductor processing chamber cleaning endpoint detection according to claim 23, including the step of using the $F_2$ emission rate plateau, or the zero slope in the $F_2$ concentration-time plot is used to indicate the endpoint.

33. A method according to claim 32, including the step of using a $NF_3$ based remote plasma downstream chamber cleaning process.

34. A method to improve the fluorine utilization efficiency in remote plasma downstream chamber cleaning according to claim 33, including the step of using $F_2$ emission from the reactor as an indicator for process optimization.

35. A method according to claim 34, including the step of using a $NF_3$ based remote plasma cleaning process, and the step of using $F_2$ emissions from a reactor high vacuum pump as an indicator for process optimization, especially, for enhancing fluorine utilization efficiency in the chamber cleaning process.

36. A method for controlling a semiconductor manufacturing processes by monitoring the concentration of homonuclear diatomic halogen gases in a process effluent gas stream comprising the steps of:
  withdrawing a sample of said effluent gas stream containing said halogen gases;
  introducing said sample of said gas stream into a sample cell having first and second ends containing windows to transmit ultra violet and visible light through said sample;
  passing said light through said sample cell and detecting light absorption by halogen gases in said cell;
  analyzing a selected absorption spectrum at selected wavelengths;
  performing spectrum analysis to determine type and concentration of halogen gases present in said effluent stream; and
  using data from spectrum analysis to control the operating parameters of the process.

37. A method according to claim 36, including the step of using a spectrometer control, data acquisition and data analysis system to analyze said absorption spectrums.

38. A method according to claim 37, including the step of using one of a personal computer or a notebook personal computer with an A/D card to analyze said absorption spectrums.

39. A method according to claim 36, including the step of fabricating said sample cell from a passivated stainless steel tube with windows/viewports know to be transparent in the UV-visible range disposed on either end of said tube.

40. A method according to claim 39, including the step of monitoring and controlling temperature and pressure inside said cell.

41. A method according to claim 36, including the step of withdrawing one of, a part, or a substantial part of the effluent flow from an effluent pipeline as said sample.

42. A method according to claim 41, including the step of extracting an effluent sample via a slip-stream sampling system through a sampling pump.

43. A method according to claim 42, including the step of controlling extraction flow rate and cell gas pressure by an upstream throttle valve and a downstream throttle valve.

* * * * *